United States Patent [19]
Julien et al.

[11] Patent Number: 5,869,718
[45] Date of Patent: Feb. 9, 1999

[54] HOMOLOGOUS RECOMBINATION FOR ANIMAL MODEL EXHIBITING REDUCED LEVELS OR ELIMINATION OF A NEURONAL INTERMEDIATE FILAMENT PROTEIN

[76] Inventors: Jean-Pierre Julien, 571 Rue Goumod, Montreal, Quebec H2R 1C1; Qinzhang Zhu, 4396 Richard, Pierrefonds, Quebec H9H 2R5, both of Canada

[21] Appl. No.: 683,601

[22] Filed: Jul. 15, 1996

[51] Int. Cl.⁶ .............................. C12N 5/00; C12N 15/00
[52] U.S. Cl. ...................... 800/2; 435/172.3; 800/DIG. 1
[58] Field of Search .............................. 800/2, DIG. 1–6; 435/172.3

[56] References Cited

PUBLICATIONS

McCall et al., "Targeted deletion in astrocyte intermediate filament (Gfap) alters neuronal physiology," *Proc. Natl. Acad. Sci.*, USA, vol. 93, pp. 6361–6366, Jun. 1996.

Colucci–Guyon et al., "Mice Lacking Vimentin Develop and Reproduce without an Obvious Phenotype," *Cell*, vol. 79, pp. 679–694, Nov. 18, 1994.

Galou et al., "Disrupted Glial Fibrillary Acidic Protein Network in Astrocytes from Vimentin Knockout Mice", *The Journal of Cell Biology*, vol. 133, No. 4, May 1996, pp. 853–863.

Friedman et al, Transgenic mouse approaches for analysis of the nervous system, NeuroProtocols, vol. 3, No. 1, pp. 69–80, Aug. 1993.

Eyer et al, Neurofilament–deficient axons and perikaryal aggregates in viable transgenic mice expressing a neurofilament–beta–galactosidase fusion protein, Neuron, vol. 12, No. 2 pp. 389–405, Feb. 1994.

Plummer et al, Accelerated and widespread neuronal loss occurs in motor neuron degeneration (mnd) mice expressing a neurofilament–disrupting transgene. Mol, and Cell. NeuroSci., vol. 6, No. 6, pp. 532–543, Dec. 1995.

Mansour et al, Disruption of the proto–oncogene int–2 in mouse embryo–derived stem cells: a general strategy for targeting mutations to non–selectable genes. Nature, vol. 336, pp. 349–352, Nov. 24, 1988.

*Primary Examiner*—Jasemine C. Chambers
*Assistant Examiner*—Deborah J. R. Clark

[57] ABSTRACT

Transgenic non-human mammals and methods of preparing such mammals are disclosed. Homologous recombination is employed to inactivate genes, particularly genes coding for neuronal intermediate filaments. These animals, whose phenotype is characterized by reduced or eliminated levels of a neuronal intermediate filament, are useful as models for studying aging, injury to the nervous system, and pathogenesis of neurodegenerative diseases. They are also useful for the screening of potential therapeutic agents.

6 Claims, 11 Drawing Sheets

NF-M

NF-L

Sciatic Nerve | Facial Nerve
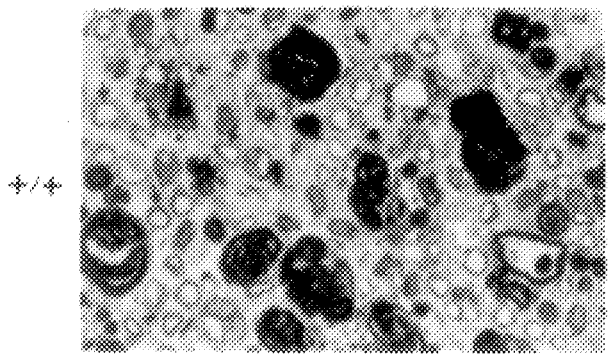 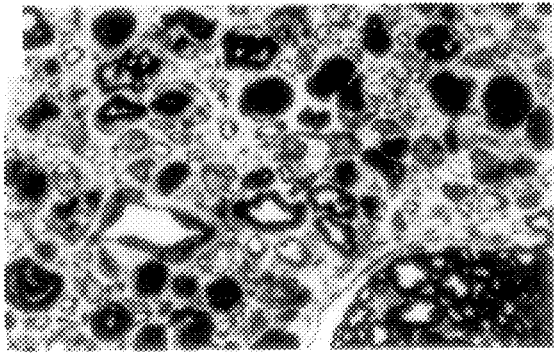
FIG. 7A | FIG. 7B
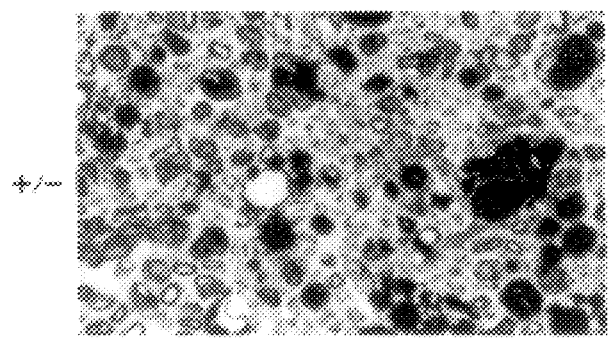 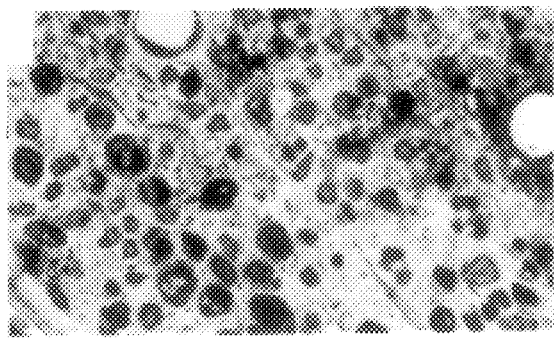
FIG. 7C | FIG. 7D
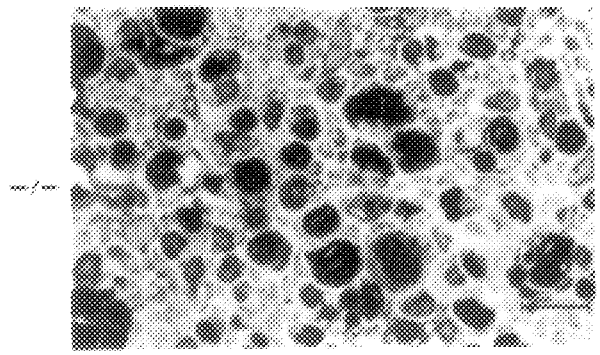 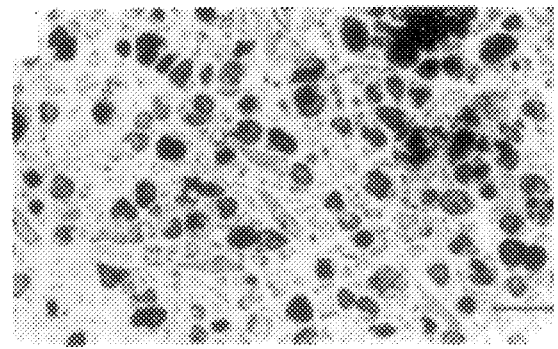
FIG. 7E | FIG. 7F

HOMOLOGOUS RECOMBINATION FOR ANIMAL MODEL EXHIBITING REDUCED LEVELS OR ELIMINATION OF A NEURONAL INTERMEDIATE FILAMENT PROTEIN

FIELD OF THE INVENTION

The present invention relates to mice into which foreign DNA has been introduced, thereby generating transgenic mice. More specifically, the invention concerns the use of homologous recombination techniques to generate mice that have reduced or eliminated levels of a neuronal intermediate filament protein.

BACKGROUND OF THE INVENTION

Neurons are important cells in the nervous system, being involved in receiving, organizing, and transmitting information. Each neuron contains a cell body, an axon (a thin, tube-like process that arises from the cell body and travels some distance before terminating), and dendrites (neuronal processes of the cell body that are shorter and thicker than axons). The cytoskeleton of the neuron provides mechanical strength to the axons and dendrites and a track for transport of materials between the cell body and the nerve terminal. The cytoskeleton is a system of interconnected macromolecular filaments. Three polymeric structures form the basis of this cytoskeleton: actin filaments (microfilaments), microtubules, and intermediate filaments.

Intermediate filaments (IFs) are 10 nm filaments that are found in most eukaryotic cells. There are six classes of IFs recognized according to sequence homology and gene structure: type I and II IFs include the acidic, neutral, and basic keratins; type III IFs include vimentin, desmin, the glial fibrillary acidic protein (GFAP), peripherin, and plasticin; type IV IFs include neurofilament proteins and α-internexin; type V IFs include the nuclear lamins; and type VI IFs include nestin expressed in neuroepithelial cells.

Neuronal intermediate filaments (NIFs) include peripherin, α-internexin and neurofilaments. The NIF proteins are encoded by a large multigene family displaying cell and tissue-specific expression patterns throughout development. For example, during embryonic development in neurons, α-internexin and peripherin are expressed at high levels, which decline as the levels of neurofilament proteins increase in the postnatal period during maturation of nerve cells.

The NIF proteins are made up of an assembly of protein subunits. The current model of NIF assembly involves 1) the bonding of two subunits to form a dimer; 2) the aggregation of two antiparallel dimers to form a tetramer, called a protofilament; 3) the joining of about eight protofilaments end on end; and 4) the association of these joined protofilaments to other joined protofilaments by staggered overlaps to form a 10 nm filament. Moreover, the cytoplasmic NIF proteins share a homologous central region of similar size (approximately 310 amino acids) flanked by amino- and carboxy-terminal domains varying greatly in sequence and in length. The central region of NIF proteins forms an extended α-helical rod domain that plays a critical role in protein assembly into 10 nm filaments.

Of all the NIF proteins that participate in the formation of the neuronal cytoskeleton, the neurofilament triplet proteins are the most abundant. These neurofilament proteins (NFs) are expressed exclusively in neurons. NFs are found predominantly in axons, where they run longitudinally and parallel to each other. NFs are formed by the copolymerization of three NF protein subunits: light (61 kDa)(NF-L), medium (90 kDa)(NF-M), and heavy (110 kDa)(NF-H). NF-L subunits form the core of the NF and are essential for NF assembly. NF-M and NF-H subunits form side-arm projections in the NF structure, cross-linking NFs and other neuronal structures into a three-dimensional IF matrix. The NF-M and NF-H projections appear to modulate the spacing between NFs, regulating the caliber of axons.

The three different NF subunits are encoded by three different genes, each of which is under separate developmental control. Significant expression of NF-L and NF-M is first seen in the embryonic brain, while in most neurons, NF-H expression is delayed relative to the other subunits and occurs in the post-natal period.

Neurofilaments and Neurodegenerative Diseases:

Neurofilaments have been linked to a number of neurodegenerative diseases. Large motor neurons are particularly vulnerable to NF abnormalities because of their high NF content and their long axons. Abnormal depositions of NFs is a phenomenon observed in many neurodegenerative diseases (Table 1).

TABLE 1

Human Diseases with Abnormal NF Accumulations

| Disease | Abnormalities | Prevalence |
| --- | --- | --- |
| ALS | NF depositions in motor neurons Decline of 60% in NF-L mRNA | 70% of cases |
| Parkinson's disease | Lewy bodies in substantia nigra and locus coeruleus Declines of 30% NF-L mRNA and 70% NF-H mRNA | 100% of cases |
| Alzheimer's disease | Cortical Lewy bodies Decline of 70% in NF-L mRNA | 20% of cases |
| Lewy body Dementia | Cortical Lewy bodies | |
| Guam-Parkinsonism | NF depositions in motor neurons | 100% of cases |
| Giant Axonal Neuropathy | NF accumulations in peripheral axons | |
| Peripheral Neuropathies | NF accumulations in peripheral axons that can be induced by various toxic agents, such as IDPN, hexanedione, acrylamide | |

As an example, there is evidence that deregulation of neurofilament expression may play a central role in motor neuron diseases such as amyotrophic lateral sclerosis (ALS). ALS is an adult-onset neurological disorder resulting from the degeneration of motor neurons in the brain and spinal cord. This leads to denervation atrophy of skeletal muscles and, ultimately, to paralysis and death.

A characteristic pathological finding in ALS patients is the presence of abnormal neurofilament accumulation in the axons of spinal motor neurons. Evidence suggests that NF accumulation may cause axonal degeneration by impeding transport of components required for axonal maintenance. Aberrant neuronal swellings that are highly reminiscent of those found in ALS have recently been reported in transgenic mice overexpressing either the NF-L or NF-H gene.

As additional evidence for NF involvement in ALS, a recent report has revealed that there is a 60% decrease in levels of NF-L mRNA in the motor neurons of patients with ALS (Bergeron et al., (1994) *Brain Res.* 659:272–276). As well, mutant NF-H alleles have been found in some ALS patients (Figlewicz et al. (1994) *Hum. Molec. Genet.* 3:1757–1761).

NFs are also implicated in Parkinson's disease. The pathological hallmark of idiopathic Parkinson's disease is the presence of Lewy bodies (LBs), cytoplasmic inclusions made up of altered NF proteins. These LBs are located in neurons of the substantia nigra. A subset of demented elderly patients also exhibit LB-like inclusions in their cortical neurons. The mechanisms involved in the abnormal aggregation of NF proteins to form LBs are still unknown. It has been found that levels of NF-L and NF-H mRNAs in substantia nigra neurons are reduced in Parkinsonian patients as compared to age-matched controls. There is also reduced NF synthesis in LB-containing neurons.

In patients with Alzheimer'disease, cortical LBs are present in approximately 20% of cases. It has also been discovered that there is a 70% decrease in NF-L mRNA expression in these patients. (Crapper McLachlan et al., (1988) *Molec. Brain Res.* 3:255–262)

The mechanisms underlying the abnormal aggregation of NF proteins in disease are still unknown. It is very interesting, however, that decreased levels of NF mRNAs are associated with degenerative neurons in ALS, Parkinson's disease, Alzheimer's disease, and other neurodegenerative diseases. Whether down-regulating NF gene expression can directly contribute to formation of NF depositions or to other pathological changes in specific populations of neurons remains to be determined.

Neurofilaments and Aging:

Aging is a factor that may contribute to axonal atrophy. There is a normal decline (50–60%) in NF mRNA expression with aging. (Parhad et al., (1995) *J. Neurosci. Res.* 41:355–366) The resulting decrease in NFs may be linked to axonal atrophy and a reduced capacity for compensatory axonal outgrowth during aging. Methods of enhancing neuronal regeneration could attenuate the aging process.

Neurofilaments and Injury:

Following injury in mammals, peripheral nervous system (PNS) axons have the capacity to regenerate, whereas central nervous system (CNS) neurons have limited axonal outgrowth. It is widely believed that NFs are not required for axonal regeneration following injury. This notion is based on the observation that neurofilament mRNAs decrease two to threefold following axotomy. Although NFs are present in the CNS, their numbers, which are much lower than in the PNS, may not be sufficient to sustain axonal outgrowth.

Animal Models:

A number of animal models for neurodegenerative diseases have been created. Transgenic mice have been generated that overexpress NF genes. In one instance, transgenic mice carrying multiple copies of the human NF-H gene were created (F. Côté, J. -F. Collard, and J. -P. Julien, (1993) *Cell* 73:35—46; J. -F. Collard, F. Côté, and J. -P. Julien, (1995) *Nature* 375:61–64). These mice progressively develop physiological and pathological features reminiscent of ALS. They are characterized by the presence of abnormal NF accumulations in the perikarya and proximal axons of spinal motor neurons. With age, motor dysfunction progresses by the atrophy and subsequent degeneration of axons distal to the NF swellings. As well, there is a dramatic reduction in rates of axonal transport of all NF proteins and other proteins, including tubulin and actin.

Other transgenic mice have been created that overproduce normal and mutant NF-L proteins (Xu et al. (1993) *Cell* 73:23–33; Lee et al. (1994) *Neuron* 13:975:988). These mice develop motor neuron degeneration accompanied by the accumulation of neurofilaments in spinal motor neurons.

A transgenic mouse has been created that expresses a fusion protein in which the carboxyl terminus of NF-H was replaced by beta-galactodisase (J. Eyer and A. Peterson, (1994) *Neuron* 12:389–405). The resulting axons develop small calibers.

A transgenic mouse has been engineered that expresses a mutant form of the human copper-zinc superoxide dismutase (SOD)(Gurney et al., (1994) *Science* 264:1772–1775). This mutation is responsible for 2% of ALS cases. The mechanism by which SOD mutants induce selective vulnerability to degeneration of motor neurons in familial ALS is unknown; however, NF accumulation and abnormalities in degenerating motor neurons have been reported.

Transgenic mouse models that overexpress wild-type or mutant NF genes have provided evidence that NF accumulations can play a causal role in motor neuron disease. It seems paradoxical, however, that levels of NF mRNAs are not increased; rather, they are reduced in patients with neurodegenerative diseases, including ALS, Parkinson's disease, and Alzheimer's disease. This suggests that NF depositions in neurodegenerative diseases might be induced by perturbations in the stoichiometry of assembled NF subunits; accordingly, there is a need for an animal model having disrupted NF genes.

A number of animal models having decreased amounts of neurofilaments have been reported. A mutant strain of quail has been discovered that is lacking NF-L subunits and is deficient in NFs (Yamasaki et al (1992) *Lab. Invest.* 66:734–743; Yamasaki et al. (1991) *Acta Neuropathol.* 82:427–434). As well, a canine model of motor neuron disease has been shown to have NF accumulations in motor neurons and a low ratio of NF-L to NF-H mRNAs (Murna and Cork, (1993) *Lab Invest.* 69:436–442).

Homologous recombination may be employed for inactivation or alteration of genes in a site-directed manner. A number of papers describe the use of homologous recombination in mammalian cells, including human cells. Illustrative of these papers are Kucherlpati et al. (1984) *Proc. Natl. Acad. Sci. USA* 81:3153–3157; Kucherlapati et al. (1985) *Mol. Cell. Bio.* 5:714–720; Smithies et al. (1985) *Nature* 317:230–234; Wake et al. (1985) *Mol. Cell. Bio.* 8:2080–2089; Ayares et al. (1985) *Genetics* 111:375–388; Ayares et al. (1986) *Mol. Cell. Bio.* 7:1656–1662; Song et al. (1987) *Proc. Natl. Acad. Sci. USA* 84:6820–6824; Thomas et al. (1986) *Cell* 44:419–428; Thomas and Capecchi (1987) *Cell* 51:503–512; Nandi et al. (1988) *Proc. Natl. Acad. Sci. USA* 85:3845–3849; and Mansour et al. (1988) *Nature* 336:348–352. Various aspects of using homologous recombination to create specific genetic mutations in embryonic stem cells and to transfer these mutations to the germline have been described (Evans and Kaufman (1981) *Nature* 294:154–146; Doctschman et al., (1987) *Nature* 330:576–578; Thomas and Capecchi (1987) *Cell* 51:503–512; Thompson et al. (1989) *Cell* 56:316–321. The combination of a mutant polyoma enhancer and a thymidine kinase promoter to drive the neomycin gene has been shown to be active in both embryonic stem cells and EC cells by Thomas and Capecchi, supra, 1987; Nicholas and berg (1983) in *Teratocarcinoma Stem Cell,* eds. Siver, martin and Strikland (Cold Spring Harbor Lab., Cold Spring Harbor, N.Y. (pp. 469–497); and Linney and Donerly, *Cell* 35:693–699, 1983.

There are, however, no animal models in which the different NF subunits are completely absent. The present invention is directed towards overcoming this void. The role of each NF subunit in the assembly and function of NFs is poorly understood. A significant need remains for an animal model to determine the specific role of each NF subunit in neuronal structure and function, to test the possibility that perturbations in the stoichiometry of NF subunits might induce abnormal NF depositions, and to further investigate the mechanisms underlying NF-induced pathology.

This background information is provided for the purpose of making known information believed by the applicant to be of possible relevance to the present invention. No admission is necessarily intended, nor should be construed, that any of the preceding information constitutes prior art against the present invention. Publications referred to throughout the specification are hereby incorporated by reference in their entireties in this application.

SUMMARY OF THE INVENTION

To meet the needs noted above, a knockout animal model has been created wherein one or more neuron-specific neuronal intermediate filament genes have been disrupted. In particular, NF knockout mice will provide a model for determining the role of each NF subunit in NF assembly and organization and in axonal transport. Knockout mice can also be used to determine whether an alteration in NF protein stoichiometry causes human neurodegenerative diseases.

One embodiment of the present invention provides for a method of producing a genetically engineered mouse having a phenotype characterized by the substantial absence of a neuron-specific neuronal intermediate filament protein otherwise naturally occurring in mice, said phenotype being conferred by said method comprising: (a) transforming mouse embryonic stem cells with a DNA construct comprising a marker gene and at least 100 bp of DNA sequence homologous with a sequence of the endogenous neuronal intermediate filament present in a chromosome of said embryonic stem cells, where said construct becomes integrated into said chromosome by homologous recombination, thereby inactivating said neuronal intermediate filament gene; (b) selecting for mouse embryonic stem cells which carry said inactivated neuronal intermediate filament gene to provide selected cells; (c) introducing the transformed embryonic stem cells into the blastocyst of a developing mouse embryo; (d) allowing the embryo to develop to term; (e) identifying at least one offspring which carries said inactivated neuronal intermediate filament gene in the germ line; and (f) breeding said offspring to produce a homozygous or heterozygous mammal lacking normal levels of a functional neuronal intermediate filament protein.

Another embodiment of the present invention involves a genetically engineered mouse having a phenotype characterized by the substantial absence of a neuron-specific neuronal intermediate filament protein otherwise naturally occurring in mice, said phenotype being produced as a result of: (a) inactivating a neuronal intermediate filament gene that is predominantly expressed in neurons via homologous recombination in an embryonic stem cell; (b) introducing said cell into the blastocyst of a developing mouse embryo; (c) allowing said embryo to develop to term; (d) identifying at least one offspring which carries said inactivated neuronal intermediate filament protein; and (e) breeding said offspring to produce a homozygous or heterozygous mouse lacking in levels of a neuronal intermediate filament protein.

In a further embodiment, these knockout animals can be used as models to study the pathogenesis of neurodegenerative diseases.

In another embodiment, these animals can be used to assess the contribution of intermediate filaments to disease mechanisms.

In another embodiment, these animals can be used as models to study aging and injury.

In another embodiment, these knockout animals can be manipulated pharmacologically to screen therapeutic agents aimed at treating neurodegenerative diseases.

In yet another embodiment, these animals can be used to screen compounds for their ability to affect levels of intermediate filaments and alter NF organization.

In yet a further embodiment, these animals can e used to study the compensatory mechanisms of axonal regeneration and to identify other intrinsic factors affecting this regeneration.

Various other objects and advantages of the present invention will become apparent from the detailed description of the invention.

DETAILS OF THE INVENTION

Figure 1A:
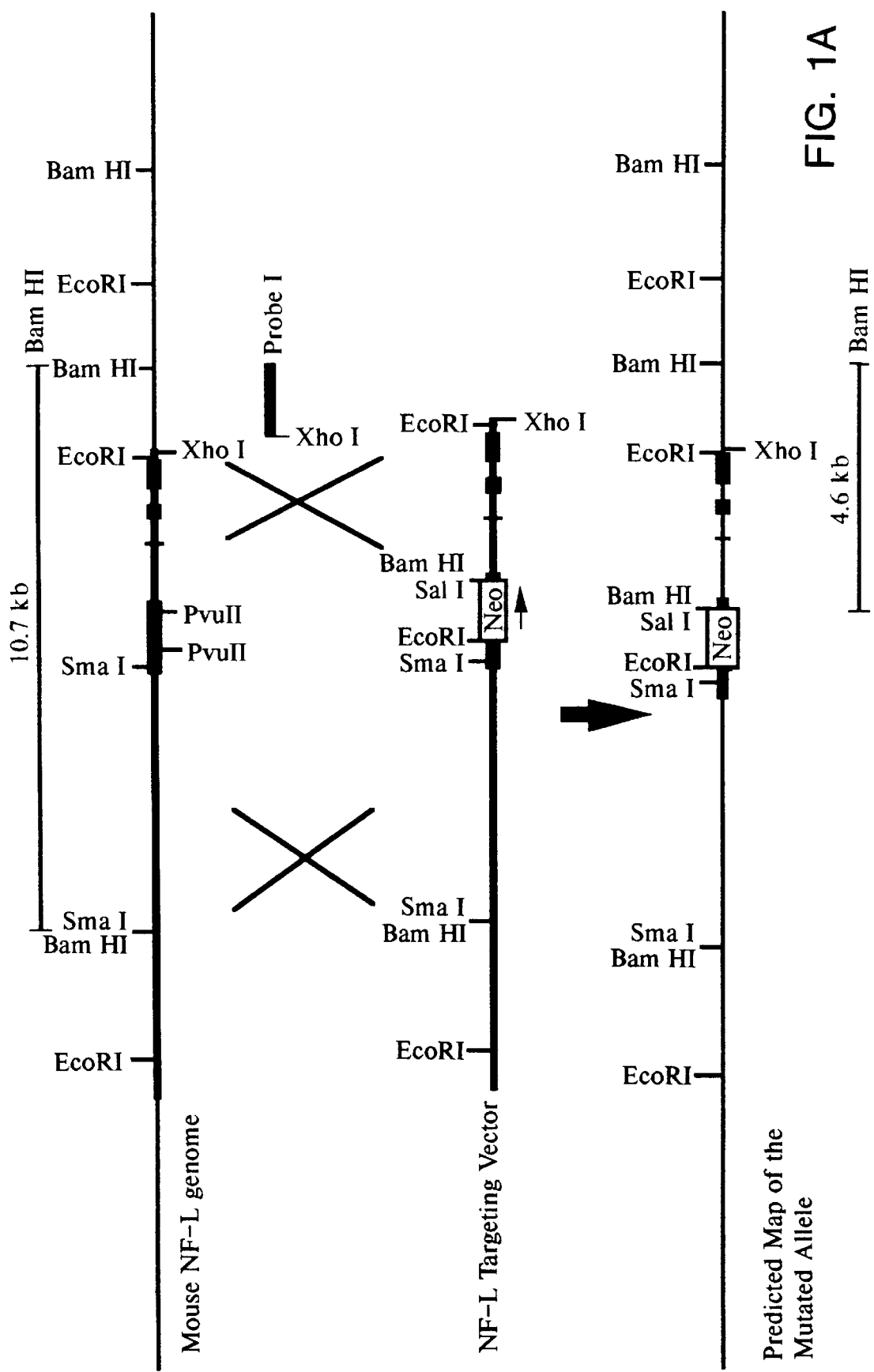
FIGS. 1A–1B. Targeted disruption of the NF-L Gene. (A) Restriction map of the mouse genomic NF-L gene, the NF-L targeting vector, and the mutated mouse NF-L allele following homologous recombination. The homologous flanking regions are shown as thicker lines, exons appear as dark boxes, and the neomycin resistance gene is represented by an open box (Neo). A 720 base-pair (bp) Pvu II-fragment from exon I of the NF-L gene was replaced by a 1.1 kilobase (kb) neo cassette from pMC1NEOpolyA. In the targeting vector, this replacement DNA is flanked by an 8 kb 5'-promoter and a 3.1 kb 3'-end compassing part of exon I and whole of exons II, III, and IV. (b) Southern blot analysis of Bam HI-digested DNA from the tails of mice, probed using a 1.5 kb Xho I-Bam HI fragment (as shown in A). the 10.7 kb Bam HI fragment is from the native allele while the 4.6 kb Bam HI fragment is from the mutated NF-L allele following homologous recombination. The symbol –/– represents mice homozygous for the replacement DNA; +/– represents heterozygous mice; and +/+ represents control mice.

The following terms and abbreviations are used throughout the specification and in the claims:
ALS refers to amyotrophic lateral sclerosis,
ES refers to embryonic stem,
LBs refers Lewy bodies,
NF-L refers to neurofilament light subunit,
NF-M refers to neurofilament medium subunit,
NF-H refers to neurofilament heavy subunit,
NIF refers to neuronal intermediate filaments, The term "neuron-specific neuronal intermediate filament" means intermediate filaments expressed predominantly in neurons including, but not limited to, NF-L; NF-M; NF-H; alpha-internexin; and peripherin. For example, vimentin is not included in this group because it is also expressed in astrocytes to a significant extent.

The term, "gene-knockout" animal refers to a mouse that has been produced suing ES cells made by selecting for a DNA insertion that replaces the chosen gene by an artificially altered version, wherein the progeny animals carry the mutation in their germ cells.

The present invention resides in the discovery that homologous recombination techniques may be employed for inactivation or alterations of genes in a site-directed manner, particularly a gene associated with a neuronal intermediate in such a manner as to selectively prevent the biosynthesis of a specific neuronal intermediate filament protein. Transgenic animals generated using these techniques can be viable and fertile, possessing alterations that are stable and can be passed from generation to generation. Moreover, these novel animals are useful models for the study of, among others, aging, injury, and disorders involving altered levels of neuronal intermediate filaments.

The transgenic animals of the present invention are created using targeted gene replacement, a sequence by which a specific DNA sequence of interest (target DNA) is replaced by an altered DNA (replacement DNA). The genome of animal embryonic stem (ES) cells is modified using homologous recombination. (Capecchi (1989) Science 244:1288; See U.S. Pat. No. 5,487,992).

Briefly, a vector is constructed that carries the replacement DNA. Both ends of the replacement DNA are flanked by long DNA sequences homologous to the sequences flanking the target DNA. When the vector is introduced into ES cells, the homologous sequences align and recombination may take place. This results in the target DNA being exchanged for the replacement DNA. The frequency of homologous recombination is low; thus, a screening system is used. The replacement DNA will contain a positive marker sequence, usually a neomycin resistance gene; thus, any cells that incorporate the replacement DNA by homologous recombination will resist neomycin. By growing cells in medium containing the drug neomycin one can select only those cells containing the replacement DNA by Southern blot analysis. The ES cells containing the replacement DNA are then inserted into recipient mouse embryos to create chimeric mice. Chimeras with germ cells derived for the altered ES cells transmit the modified genome to their offspring, yielding mice heterozygous for the target DNA (contain one target DNA and one replacement DNA). The heterozygotes are then bred with each other to create mice homozygous for the replacement DNA and deficient in the target DNA.

The DNA will comprise at least a portion of the gene(s) at the particular locus with introduction of a lesion into at least one, usually both copies, of the native gene(s), so as to prevent expression of a functional NIF molecule. The lesion may be an insertion, deletion, replacement or combination thereof. When the lesion is introduced into only one copy of the gene being inactivated, the cells having a single unmutated copy of the target gene are amplified and may be subjected to a second transformation, where the lesion may be the same or different from the first lesion, usually different, and where a deletion, or replacement is involved, may be overlapping at least a portion of the lesion originally introduced. The resulting transformants are screened for the absence of the functional NIF protein of interest and the DNA of the cell may be further screened to ensure the absence of a wile-type target gene. Alternatively, homozygosity as to a phenotype may be achieved by breeding hosts heterozygous for the mutation.

The procedures employed for inactivating one or both copies of a gene coding for a particular NIF (eg. NF-L versus NF-M versus peripherin, etc.) will be similar, differing primarily in the choice of sequence, selectable marker used, and the method used o identify the absence of the NIF protein, although similar methods may be used to ensure the absence of expression of a particular NIF protein. Since the procedures are analogous, the inactivation of the NF-L gene will be used as an example. It is to be understood that substantially the same procedures, but with other genetic sequences, will suffice for the NF-M, NF-H, peripherin and alpha-internexin genes, among other neuronal intermediate filament genes.

DNA constructs may be employed which provide for the desired introduction of the lesion into the cell. The constructs may be modified to include functional entities other than the mutated sequence which may find use in the preparation of the construct, amplification, transformation of the host cell, and integration of the construct into the host cell. Techniques which may be used include calcium phosphate/DNA coprecipitates, microinjection of DNA into the nucleus, electroporation, bacterial protoplast fusion with intact cells, transfection, or the like. The DNA may be single or double stranded, linear or circular, relaxed or supercoiled DNA. For various techniques for transforming mammalian cells, see Keown et al., *Methods in Enzymology* (1990) 185:527–537.

The homologous sequence for targeting the construct may have one or more deletions, insertions, substitutions or combinations thereof. For example, the NIF gene may include a deletion at one site and an insertion at another site which includes a gene which may be used for selection, where the presence of the inserted gene will result in a defective inactive protein product. Preferably, substitutions are employed. For an inserted gene, or particular interest is a gene which provides a marker, e.g., antibiotic resistance such as neomycin resistance, including G418 resistance.

The deletion will be at least about 50 bp, or more usually at least about 100 bp, and generally not more than about 20 kbp, where the deletion will normally include at least a portion of the coding region including a portion of or one or more exons, a portion of one or more introns, and may or may not include a portion of the flanking non-coding regions, particularly the 5'-non-coding region (transcriptional regulatory region). Thus, the homologous region may extend beyond the coding region into the 5'-non-coding region or alternatively into the 3'-non-coding region. Insertions will generally not exceed 10 kbp, usually not exceed 5 kbp, generally being at least 50 bp, more usually at least 200 bp.

The homologous sequence should include at least about 100 bp, preferably at least about 150 bp, more preferably at least about 300 bp of the target sequence and generally not exceeding 20 kbp, usually not exceeding 10 kbp, preferably less than about a total of 5 kbp, usually having at least about 50 bp on opposite sides of the insertion and/or the deletion in order to provide for double crossover recombination.

Upstream and/or downstream from the target gene construct may be a gene which provides for identification of whether a double crossover has occurred. For this purpose, the herpes simplex virus thymidine kinase gene may be employed, since the presence of the thymidine kinase gene may be detected by the use of nucleoside analogs, such as Acyclovir or Gancyclovir, for their cytotoxic effects on cells that contain a functional HSV-tk gene. The absence of sensitivity to these nucleoside analogs indicates the absence of the thymidine kinase gene and, therefore, where homologous recombination has occurred that a double crossover event has also occurred.

The presence of the marker gene inserted into the NIF gene of interest establishes the integration of the target construct into the host genome. However, DNA analysis might be required in order to establish whether homologous or non-homologous recombination occurred. This can be determined by employing probes for the insert and then sequencing the 5' and 3' regions flanking the insert for the presence of the NIF of interest extending beyond the flanking regions of the construct or identifying the presence of a deletion, when such deletion in introduced.

The polymerase chain reaction may be used, with advantage in detecting the presence of homologous recombination (Kim and Smithies, (1988) *Nucleic Acid Res.* 16:8887–8903; and Joyner et al (1989) *Nature* 338:153–156). Primers may be used which are complementary to a sequence within the construct and complementary to a sequence outside the construct and at the target locus. In this way, one can only obtain DNA duplexes having both of the primers present in the complementary chains in homologous recombination has occurred. By demonstrating the presence of the primer sequences or the expected size sequence, the occurrence of homologous recombination is supported.

The construct may further include a replication system which is functional in the mammalian host cell. For the most part, these replication systems will involve viral replication systems, such as Simian Virus 40, Epstein-Barr virus, papilloma virus, adenovirus and the like.

Where a marker gene is involved, as an insert, and/or flanking gene, depending upon the nature of the gene, it may have the wild-type transcriptional regulatory regions, particularly the transcriptional initiation regulatory region or a different transcriptional initiation region. Whenever a gene is from a host where the transcriptional initiation region is not recognized by the transcriptional machinery of the mammalian host cell, a different transcriptional initiation region will be required. This region may be constituitive or inducible, preferably inducible. A wide variety of transcriptional initiation regions have been isolated and used with different genes. Of particular interest as promoters are the promoters of metallothionein-I and II from a mammalian host, thymidine kinase, beta-actin, immunoglobulin promoter, human cytomegalovirus promoters, and SV40 promoters. In addition to the promoter, the wild-type enhancer may be present or an enhancer from a different gene may be joined to the promoter region.

The construct may further include a replication system for prokaryotes, particularly *E. coli,* for use in preparing the construct, cloning after each manipulation, allowing for analysis, such as restriction mapping or sequencing, followed by expansion of a clone and isolation of the plasmid for further manipulation. When necessary, a different marker may be employed for detecting bacterial transformants.

Once the vector has been prepared, it may be further manipulated by deletion of the bacterial sequences as well as linearization, where a short deletion may be provided in the homologous sequence, generally not exceeding about 500 bp, generally being from about 50 to 300 bp. The small deletion will generally be near one or other end of the targeted structural gene.

Once the construct has been prepared and manipulated and the undesired sequences removed from the vector, e.g., the undesired bacterial sequences, the DNA construct is now ready to be introduced into the target cells. As already indicated, any convenient technique for introducing the DNA into the target cells may be employed. After transformation of the target cells, many target cells are selected by means of positive and/or negative markers, as previously indicated, neomycin resistance and Acyclovir or Gancyclovir resistance. Those cells which show the desired phenotype may then be further analyzed by restriction analysis, electrophoresis, Southern analysis, polymerase chain reaction or the like. By identifying fragments which show the presence of the lesion(s) at the target gene site, one can identify cells in which homologous recombination has occurred to inactivate the target gene.

A second construct would differ from the first construct in not necessarily requiring a marker for selection, since the absence of the target NIF protein may be used as a marker. Thus, one may again use insertions, deletions or replacements as lesions for modifying and inactivating the target gene. Similarly, using techniques known in the art, one may detect the absence of the particular NIF protein of interest as evidence of the absence of expression of the particular target NIF gene.

For embryonic stem cells, after mutation, the cells may be plated onto a feeder layer in an appropriate medium, e.g., fetal bovine serum enhanced DMEM. Cells containing the construct may be detected by employing a selective medium and after sufficient time for colonies to grow, colonies may be picked and analyzed for the occurrence of homologous recombination. As described previously, the polymerase chain reaction may be used, with primers within and without the construct sequence but at the target locus. Those colonies which show homologous recombination may then be used for embryo manipulating and blastocyst injection. Blastocysts may be obtained from 4 to 6 week old superovulated females by flushing the uterus 3.5 days after ovulation. The embryonic stem cells may then be trypsinized and the modified cells added to a droplet containing the blastocysts. At least one, usually at least about 10, and up to about 30 of the modified embryonic stem cells may be injected into the blastocoel of the blastocyst. After injection, at least one and not more than about 15 of the blastocysts are returned to each uterine horn of pseudopregnant females. Females are then allowed to go to term and the resulting litters screened for mutant cells having the construct. The blastocysts are selected for different parentage from the transformed ES cells. By providing for a different phenotype of the blastocyst and the ES cells, chimeric progeny can be readily detected. Or, one may look to genotype, probing for the presence of modified genomic DNA.

The pups will usually be born 16–18 days after introduction of the blastocysts into foster mothers. The chimeric animals are screened for the presence of the transformed genome and males and females comprising the transformed genome are mated.

The versatility of these homologous recombination methods for generating "gene-knockout" animal models for each NIF gene is demonstrated by the following general description of a preferred embodiment, particularly as described in the examples, applied to study the role of NIFs in aging, neurodegenerative disease, nervous system injury, etc. It is to be understood that while the remaining discussion is directed largely to the utility of NF-L "gene-knockout" mice, the utility of this invention is not so limited to solely this NIF protein. Rather, the following discussion is provided merely for exemplification of their versatility and preferred use.

In these types of embodiments, gene-knockout animals are created by targeted disruption of NIF genes in mice. Vectors are created in which a thymidine kinase/neomycin cassette disrupts an exon of the target gene. These vectors are inserted in ES cells, and, following homologous recombination, selected ES cells are injected into mice embryos. Chimeric mice are bred to produce knockout mice.

In a preferred embodiment, a knockout NF-L –/– mouse is created by disrupting exon I in both alleles of the NF-L gene. As a result, no NF-L subunits are produced. Mice homozygous for the disrupted NF-L gene develop no overt phenotypes and breed well. A dramatic hypotrophy of axons confirms a role of NF-L in the radial growth of axons. Unexpectedly, the levels of NF-M and NF-H subunits are also reduced in the absence of the NF-L subunit, resulting primarily from decreased protein stability and transport. Furthermore, the NF-M and NF-H proteins do not assemble into filaments in the absence of NF-L.

The examples to follow illustrate a deficient regeneration of peripheral axons in mice lacking NFs. For instance, 11 days after a crush of the sciatic nerve, the number of regenerated axons in NF-L –/– mice corresponded to 25% or less than the number found in normal mice. This scarcity of regenerated axons was even more dramatic in the facial nerve: 9 days after a crush of the facial nerve of adult mice, the number of growing axons in both NF-L –/– and NF-L +/– mice corresponded to less than 10% of the number of regenerated axons in normal mice. It is remarkable that such impairment in regeneration occurs in mice heterozygous for NF-L gene inactivation since NF-L expression is reduced by only 50% in these mice.

In another embodiment of the invention, a knockout NF-M –/– mouse is created by disrupting exon I in both alleles of the NF-M gene. This NF-M knockout mouse revealed a mild hypotrophy of axons. As well, less than 10% of the mice developed an early onset paralysis of hindlimbs.

The transgenic animals of this invention can be used as animal models to aid in developing strategies to study the requirement for neurofilaments in axonal regeneration that enhance neuronal regeneration in peripheral neuropathies and following injury in the PNS or perhaps the CNS. For example, this NF-L model was used to determine that the number of neurofilaments in an axon is a key determinant in efficient axonal regeneration, suggesting that neurofilaments may act as a mechanical support or scaffold for stabilization of growing axons.

The present knockout non-human animal model is an improvement over the current tools available for studying the role of NIFs in the pathology of neurodegenerative diseases, including ALS, Alzheimer's disease, and Parkinson's disease for a number of reasons. First, the affected neurons in these diseases have long axonal projections where NFs are predominantly found. The presence of neurofilament depositions in axons is a hallmark of these diseases. Second, recent transgenic mouse studies have shown that abnormal neurofilament accumulations can induce neurodegeneration (Cote et al. (1993) Cell; Collared et al. (1995) Nature; Xu et al. (1993) *Cell;* Lu et al. (1994) Neuron). Third, the levels of neurofilament mRNAs are reduced dramatically (by ~70% as compared to age-matched controls) in affected neurons of neurodegenerative diseases. Fourth, in NF-L knock-out mice, there is an upregulation tau and APP which are markers of Alzheimer's disease.

The present invention is described in further detail in the following non-limiting Examples. It is to be understood that the examples described below are not meant to limit the scope of the present invention. It is expected that numerous variants will be obvious to the person skilled in the art to which the present invention pertains, without any departure from the spirit of the present invention. The appended claims, properly construed, form the only limitation upon the scope of the present invention.

EXAMPLE I

Preferred Intermediate Filament Deficient Animal Model

Generating a Transgenic Knockout Animal Model Deficient in One Intermediate Filament, NF-L.

DNA Constructs:

The mouse genomic NF-L DNA fragments were isolated from a mouse 129Sv phage genomic library (kindly provided by J. Rossant, Mount Sinai Research Institute, Toronto) using a NF-L cDNA probe (Julien et al., 1986). Five partially overlapping fragments were purified, of which one encompassing the entire gene (QZ10L) was subcloned into pQZ1B, a pUC derived vector. The targeting vector pQZ10LBNeo was constructed by replacing a 700 bp Pvu II fragment from the first exon of NF-L with a 1.1 kb neo cassette from pMClneoPoly A (Stratagene) flanked by 8 kb at the 3'-end and 3.1 kb at the 5'-end. The final targeting fragment was excised by an XhoI-Not I double digestion of pQZ10LB and purified by agarose (Gibco BRL).

Figure 1B:
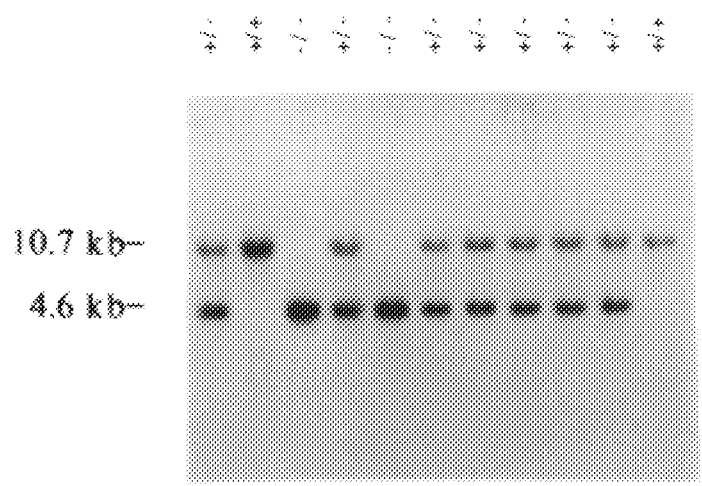

Cell Culture, Embryo Microinjection, and Animal Breeding:

The R1 ES cell culture and transfection was carried out mainly as previously described (Mansour et al., 1988; Ramirez-Solis et al., 1993). A total of 25 μg purified DNA of the targeting fragment was used to transfect 107 ES cells using a BRL Cell Porator at 3307F 230 V in DMEM medium at room temperature. G418 at 180 μg/ml was applied 24 hours post-electroporation for three days, then increased to 360 μg/ml. After 7 to 8 days of G418 selection, colonies were picked up, trypsinized, and plated onto 96-well plates with a SNL feeder layer (feede layer and LIF 1000 units/ml were used at all times in the ES cell culture). Cells were trypsinized 4 days later. 30% of the cells were plated onto gelatin-coated 96-well plates for extraction of DNA and 70% of the cells were frozen down in the same plate with frozen medium. DNA was extracted 5 days later and digested with Bam HI in the same plates (Ramirez-Solis et al., 1993). ES cell lines showing a 4.6 kb recombinant band (see FIG. 1) in the Southern blot analysis were expanded. After confirmation of reduced intensity of a 10.7 kb band with a 720 bp Pvu II fragment probe and a single 4.6 kb band with a neo 1.1 kb probe on the Southern blot, one of the ES cell lines (19F11) was injected into C47BL/6 blastocysts as described (Mansour et al., 1988; Ramirez-Solis et al., 1993). Germline transmission was obtained by mating male mosaics to C57BL/6 females. The use of animals and all surgical procedures described in this article were carried out according to The Guide to the Car and Use of Experimental Animals of the Canadian Council on Animal Care.

Western Blot Analysis:

Mice were sacrificed by intra-peritoneal injection of an overdose of pentobarbital. Sciatic nerve and brain tissues were collected, snap frozen in liquid nitrogen, and stored at −80° C. Total protein extracts were obtained by homogenization in SDS-urea extraction medium (0.05% SDS, 8M Urea in 7.4 phosphate buffer). Supernatants were collected after centrifugation at 10,000 xg for 20 minutes. The amount of proteins was estimated using a Biolab protein assay kit. Protein samples (10 μg) were loaded onto a 10% denaturing SDS-PAGE gel and electrophoresis progressed at 200 volts for 1 hour. Proteins were either visualized by Commassie blue staining or blotted onto a nitrocellulose membrane for Western blot analysis. The monoclonal antibodies against NF-L, NF-M, NF-H were purchased from Amersham; the monoclonal antibody against GAP-43 was purchased from Boehringer Mannheim.

RNA analysis

Mice were sacrificed by cervical dislocation. Following dissection, tissues were immediately frozen in liquid nitrogen and stored at −80° C. until use. Total RNA was isolated by homogenization in guanidinium thiocyanate and ultra centrifugation through a CsCl cushion (Chirgwin et al. 1979). 20 μg of each RNA sample were fractionated on a 1% agarose-formaldehyde gel (Davis et al. 1980) prior to blotting. The filter was prehybridized, hybridized with the appropriate DNA probes, and washed as previously described for Southern analysis [(Cote et al. (1993) *Cell* 73:35–46]

Histological Methods

Mice were sacrificed by an overdose of pentobarbital, perfused first with 0.9% NaCl and then with a fixative (2.5% glutaraldehyde, 0.5% paraformaldehyde in sodium phosphate buffer pH 7.4). Tissue samples were immersed in fixative for 2 hours, rinsed in phosphate buffer, and postfixed in 1% osmium tetroxide. After three washes with phosphate buffer, each sample was dehydrated in a graded series of ethanol and embedded in Epon. The thin sections were stained with toludine blue and examined under a Polyvar microscope. Axon number and the thickness of the myelin layer in the L5 ventral root were counted using the Image-1 software from Universal Imaging Corporation (Pennsylvania). The ultrathin sections were stained with uranyl acetate and lead citrate and examined with a Philips CM10 electron microscope.

For immunoreactivity studies, mice were anaesthetized by an overdose of pentobarbital and perfused first with 0.9% NaCl and then 4% paraformaldehyde in sodium phosphate buffer pH 7.4. Sciatic nerves were rinsed in phosphate buffer and immersed in a 15% sucrose and phosphate buffer. Cryostat sections of 10 μm were first incubated with first antibodies and then with FITC conjugated anti-mouse IgG antibodies. Sections were examined under a Polyvar microscope.

Characterizing an Animal Model Deficient in One Intermediate Filament

Figures 2A, 2B:
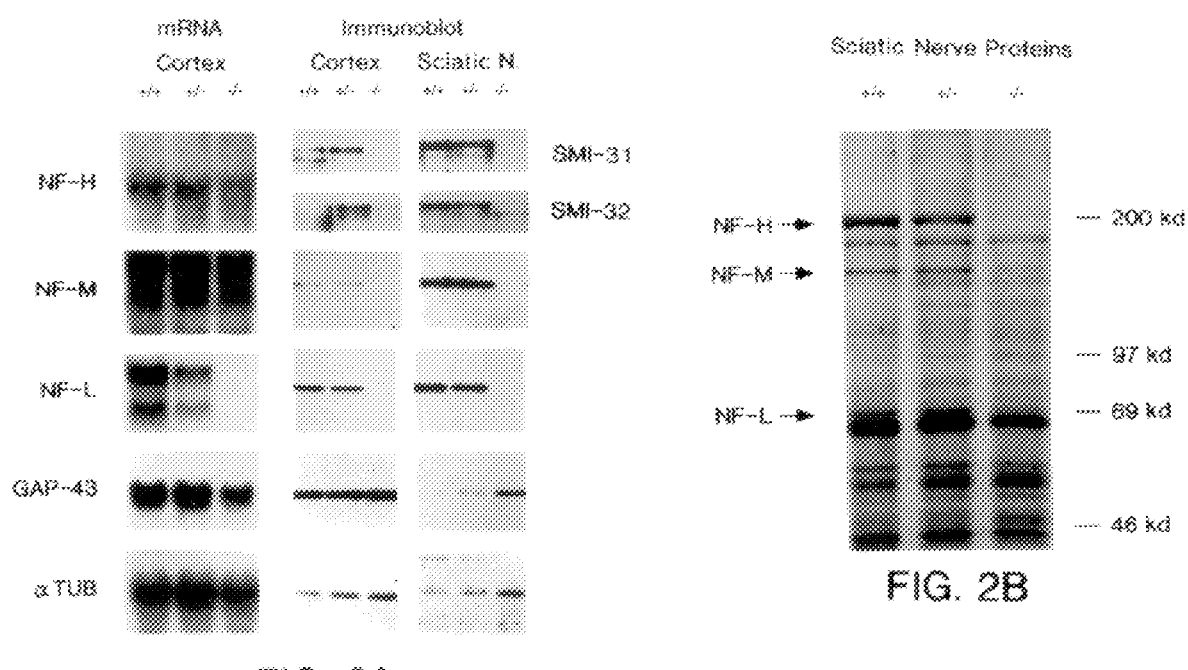
FIGS. 2A–2B. Northern blot, western blot and protein composition analysis. (A) Northern blot analysis of the cortex mRNA shows no detectable changes in mRNA levels for NF-H, NF-M, and tubulin among NF-L control (+/+), heterozygous (+/–), and homozygous (–/–) mice. The NF-L mRNA levels are about 50% lower in NF-L +/– mice as compared to a normal NF-L +/+ litter mate. GAP-43 mRNA levels are about 25% lower in the NF-L –/– mice as compared to a normal NF-L +/+ litter mate. There is no detectable NF-L mRNA in the NF-L –/– mice. Western blot analysis (Immunoblots) of cortex and sciatic nerve tissues shows that the depletion of NF-L has a profound effect on the protein levels of other cytoskeleton components. Although the levels of GAP-43 mRNA decrease in homozygous mice, an increase in protein of about 2–3 fold is noticed in homozygous mice. There is also a 4–5 fold increase in tubulin in homozygous NF-L knock-outs. A slight increase of GAP-43 and α-tubulin is also noticed in the heterozygous mice. (B) Protein composition of axons from sciatic nerve of control (+/+), heterozygous (+/–) and homozygous NF-L knockout (–/–) mice separated by SDS-PAGE and revealed by Commassie blue staining. Protein molecular weight markers are indicated on the right. Arrows point to corresponding neurofilament subunits. The decreases in NF-H, NF-M and NF-L subunits are evident in the NF-L +/– and –/– mice.
Figures 3A, 3B, 3C, 3D:
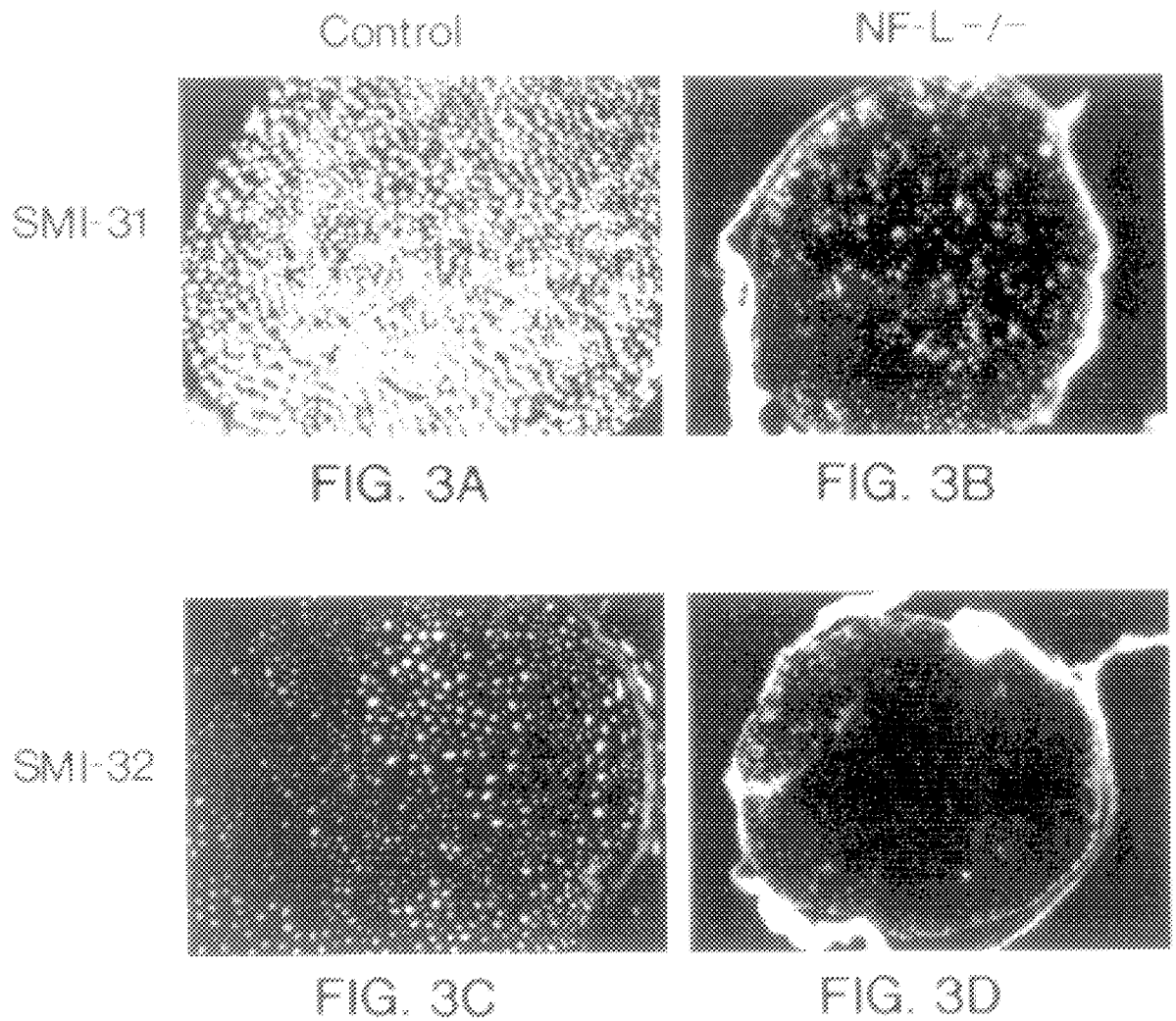
FIG. 3. Immunofluorescence detection of three neurofilament subunits in the sciatic nerve of control and NF-L –/– mice. The immunoreactivity of NF-M and phosphorylated NF-H (SMI-31) is still detected in the homozygous NF-L knock-outs (–/–) demonstrating that phosphorylation and axonal transport of NF-H and NF-M can take place in some axons in the absence of 10 nm neurofilament polymers. [Bar=50 $\mu$]
Figure 3E:
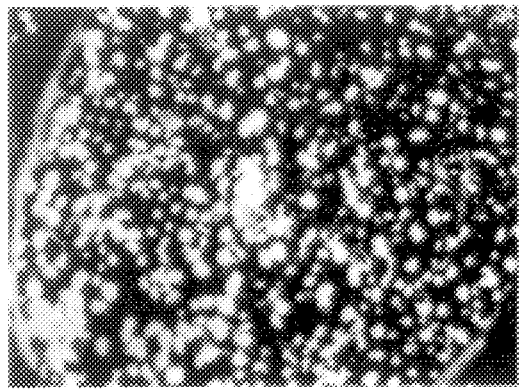
Figure 3F:
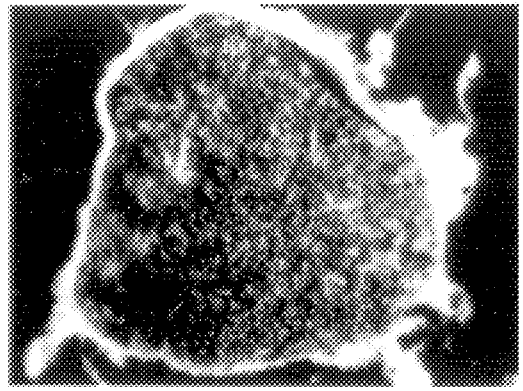
Figure 3G:
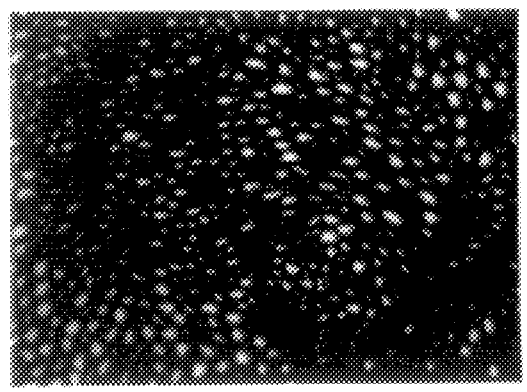
Figure 3H:
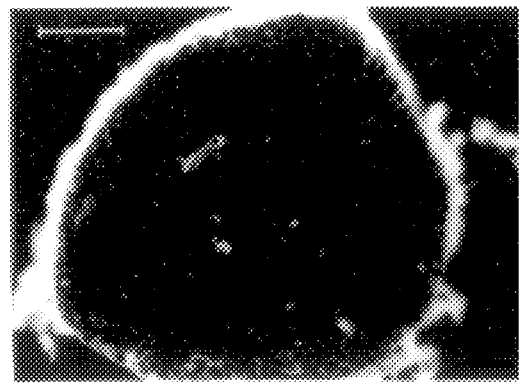

The following experiments demonstrated reduced levels of NF-M and NF-H proteins in the absence of NF-L. Northern blot analysis was carried out with 10 μg of total brain mRNA from 2 month old +/+, +/− and −/− mice (FIG. 2A). As expected, no NF-L mRNA was detected in NF-L knock-out mice; there was a 50% decrease in NF-L mRNA detected in NF-L heterozygous +/− mice. The depletion of NF-L mRNA did not affect the level of expression of either NF-M or NF-H mRNAs in NF-L +/− and −/− mice; however, the immunoblots in FIG. 2A and the Commassie blue stained gel of total proteins from the sciatic nerve revealed dramatic decreases in the levels of both NF-M and NF-H proteins in the NF-L knock-out mice. The low levels of NF-M and NF-H proteins in NF-L knock-out mice were further confirmed by immunofluorescence microscopy of the sciatic nerve using a specific anti-NF protein antibodies (FIG. 3). No staining of axons occurred with anti-NF-L antibodies. The SMI-31 antibody, which recognizes the hyperphosphorylated NF-H protein, and the anti-NF-M monoclonal (Boeringer) yielded a very weak immunofluorescence staining of sciatic axons from NF-L −/− mice as compared to those from normal mice (FIG. 3). The presence of dephosphorylated NF-H protein in the NF-L −/− axons was not detected with the SMI-32 antibody.

The following experiments demonstrated hypotrophy of neurofilament-deficient axons. Electron microscopy revealed a lack of neurofilament structures within axons of the central and peripheral nervous system in NF-L knock-out mice. This is illustrated in FIG. 4 where large myelinated axons of the adult sciatic nerve, which normally contain abundant neurofilaments (FIGS. 4A and B), are completely devoid of neurofilaments in NF-L −/− mice (FIGS. 4E and F). The most abundant cytoskeletal structures in the NF-L −/− axons are the microtubules. There is an up-regulation (about 3-fold) in the α-tubulin content of the sciatic nerve of NF-L −/− mice (FIG. 2A). We obtained evidence that the elevated levels of tubulin are not due to changes in tubulin mRNA levels but rather to an increased rate of axonal transport of tubulin in the absence of neurofilaments (data not shown).

Figure 4A:
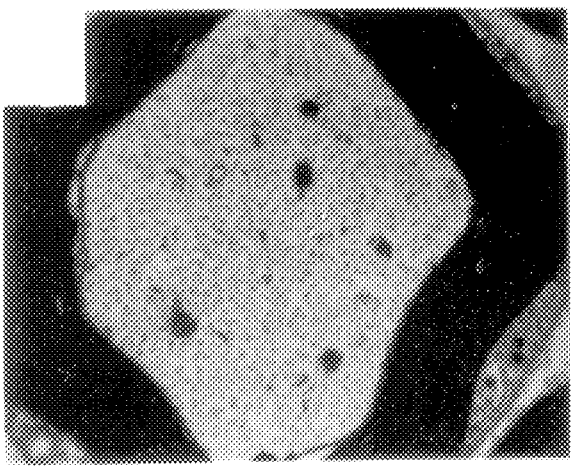
FIGS. 4A–4F. Lack of neurofilaments (NFs) in the axons of NF-L knock-out mice. Electron Microscopy of cross- (A, C, E) and longitudinal (B, D, F) sections of myelinated axons from the sciatic nerve of control +/+ (A, B), heterozygous +/– (C, D) and homozygous –/– (E, F) litter mates. In the heterozygous NF-L +/– mouse, there is a decrease of 10 nm NF density but normal caliber size and myelin layers. A complete depletion of NF-L in the NF-L –/– mice abolishes the formation of 10 nm NFs resulting in a smaller caliber size. No abnormal myelination was noticed in the NF-L –/– mouse. (x19,500)
Figure 4B:
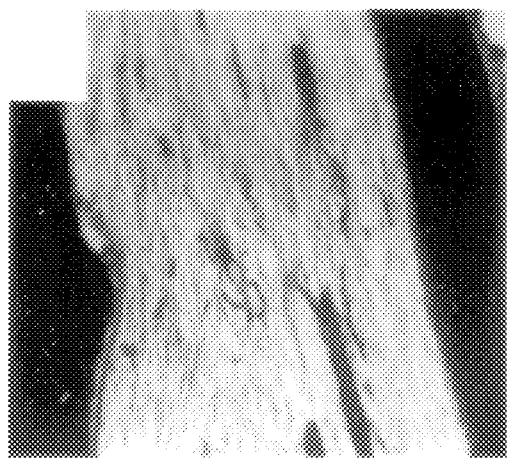
Figure 4C:
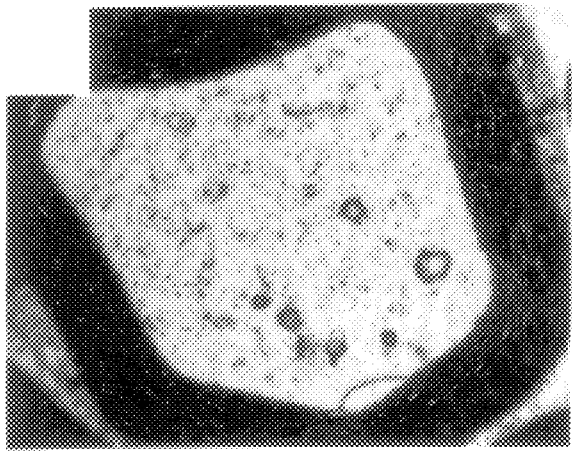
Figure 4D:
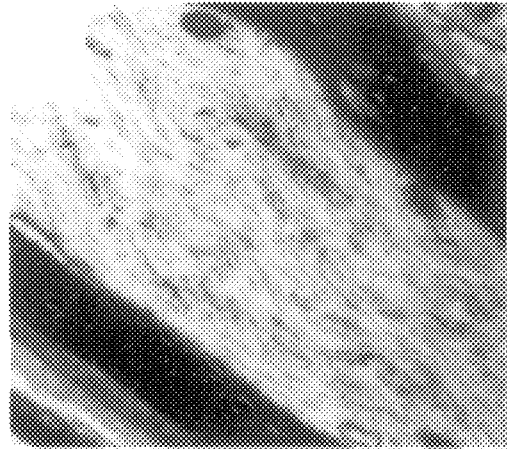
Figure 4E:
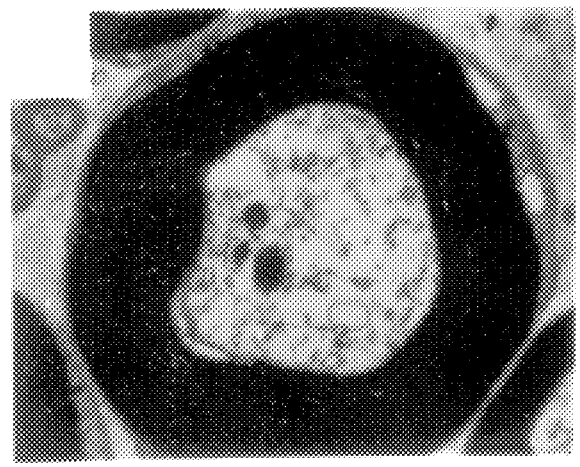
Figure 4F:
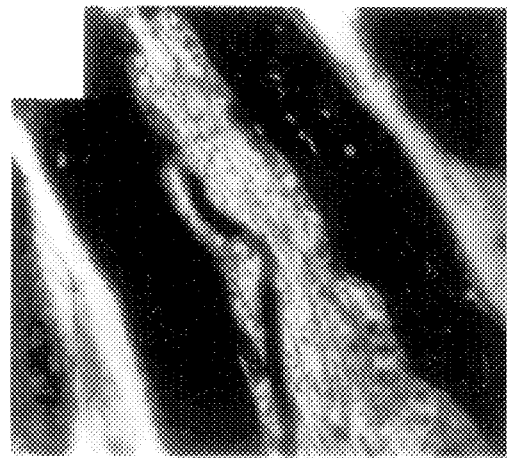
Figure 5B:
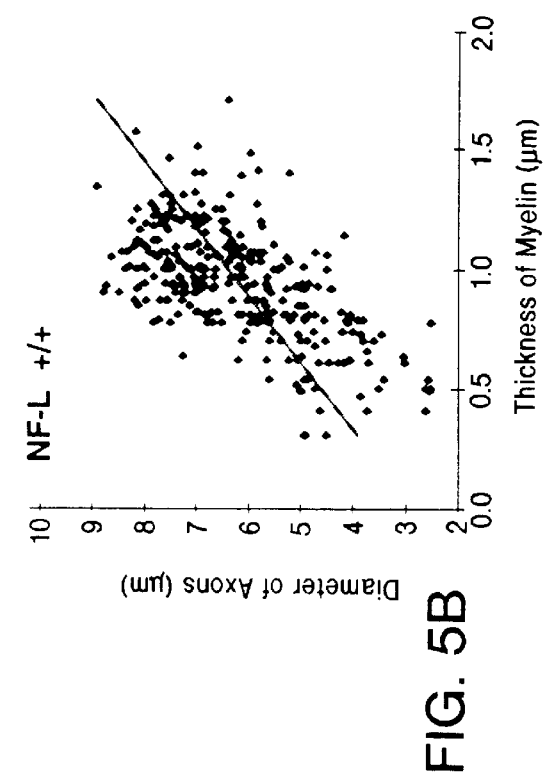
FIGS. 5(A–H). Comparisons of caliber size (A, C, E) and the thickness of myelin layers (B, D, F) of L5 ventral root axons in the NF-L knockout mice. Note the slight reduction in caliber size in the heterozygous +/– mice (C) and the absence of large motor axons in the homozygous –/– knockouts (E). Neither lower neurofilament density nor smaller caliber size affected the extent of myelination in these mice (D, F) here is a slight reduction in the total number of axons in homozygous (–/–) and heterozygous (+/–) mice (G).
Figure 5D:
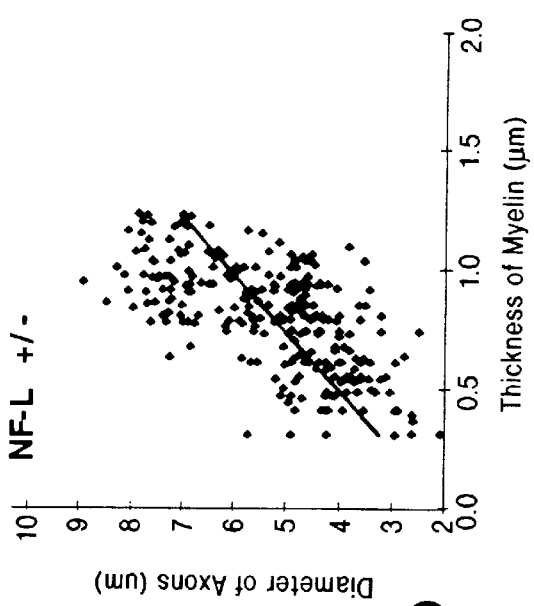
Figure 5A:
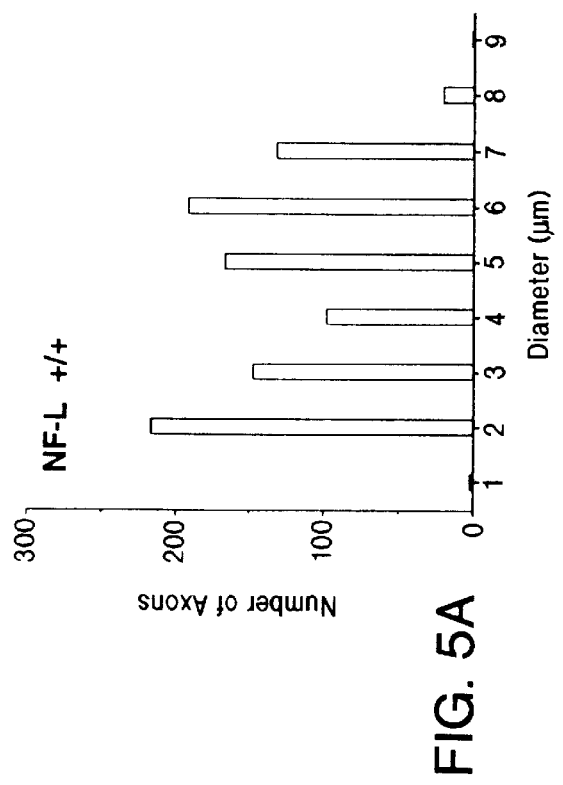
Figure 5C:
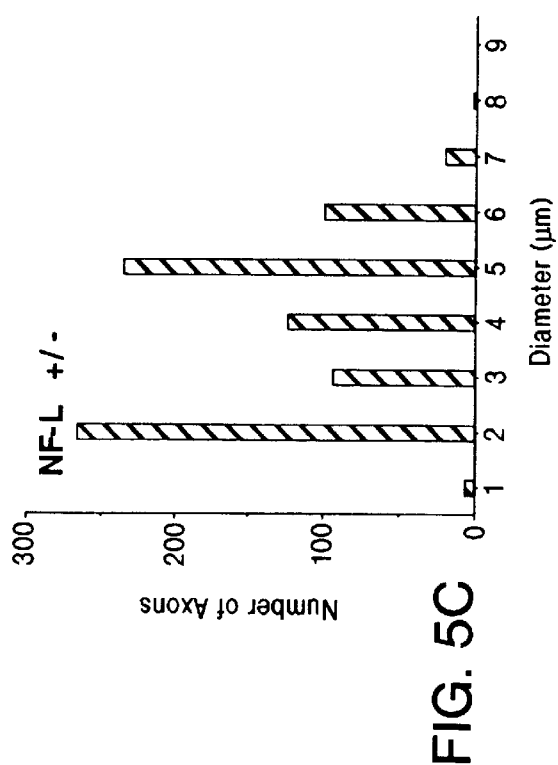
Figure 5F:
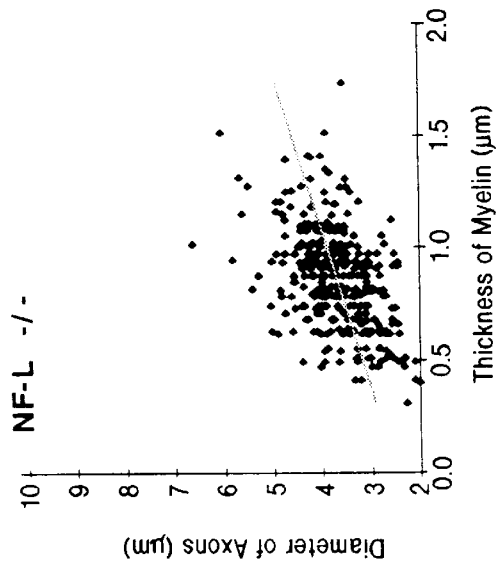
Figure 5H:
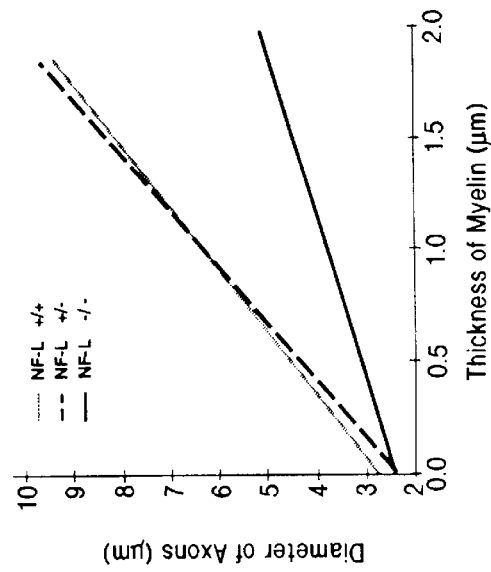
Figure 5E:
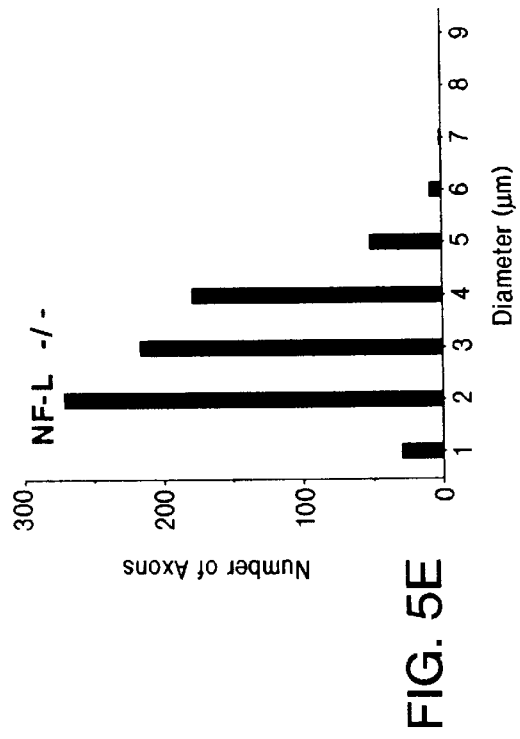
Figure 5G:
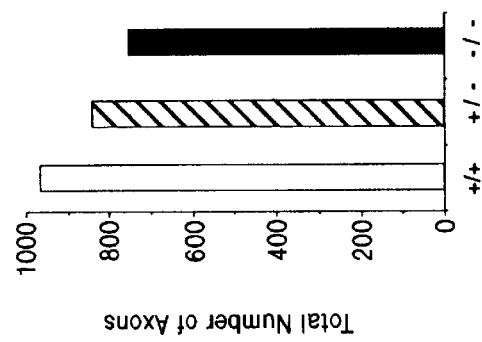

In heterozygous NF-L +/− mice, there is a decrease of approximately 50% in NF-L protein levels (FIG. 2), which generates a corresponding 50% reduction in the density of neurofilaments within axons (FIGS. 4C and D) as compared to wild-type axons (FIGS. 4A and B). To examine the effects of altered levels of neurofilaments on the radial growth of axons, axon calibers were measured in the L5 ventral roots of 2-month old mice (FIG. 5). Wild type mice showed a bimodel distribution of axonal calibers representing the small and large myelinated axons (FIG. 5A). The NF-L +/− mice also yielded a bimodel distribution of axonal calibers with their large myelinated axons (FIG. 5C) being significantly smaller in caliber (~15% smaller) than those of wild type mice (FIG. 5A). In the NF-L −/− mice, there was a unimodel distribution of axon calibers with the large-sized myelinated axons being shifted to the small-size axons (FIG. 5E). These results prove unequivocally that neurofilaments play a role in determining axonal caliber. There is, however, no direct correlation between neurofilament number and axonal diameter: a 2-fold decrease in the number of neurofilaments in NF-L +/− mice produced only a modest decrease in the axonal diameter of large myelinated axons (FIG. 5C).

Figure 6A:
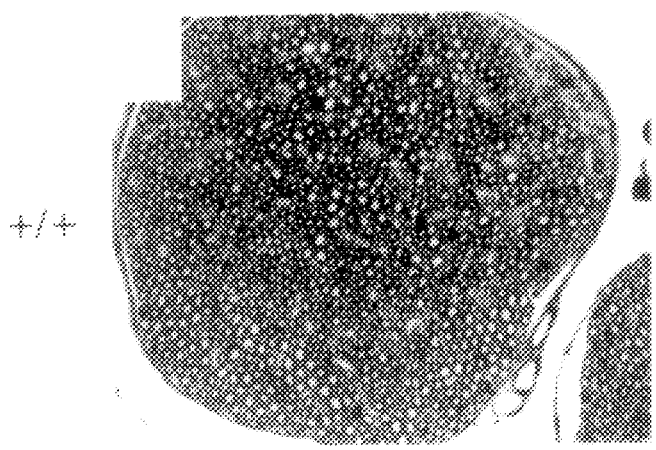
FIGS. 6(A–F). Hypotrophy of myelinated axons in the sciatic nerve.
Figure 6B:
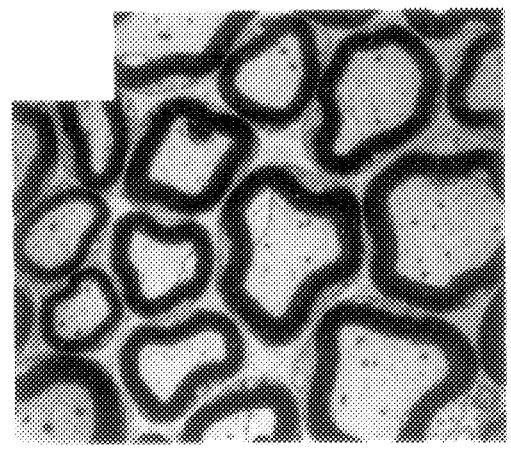
Figure 6C:
Figure 6D:
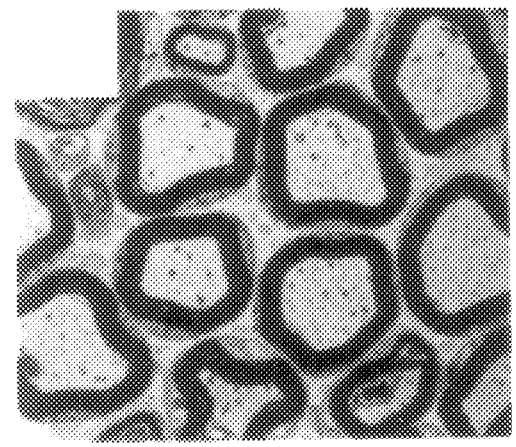
Figure 6E:
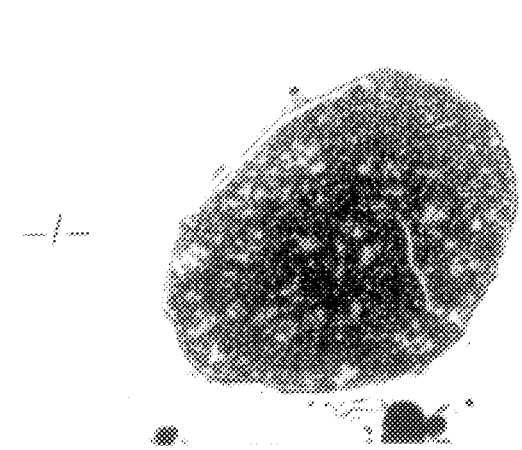
Figure 6F:
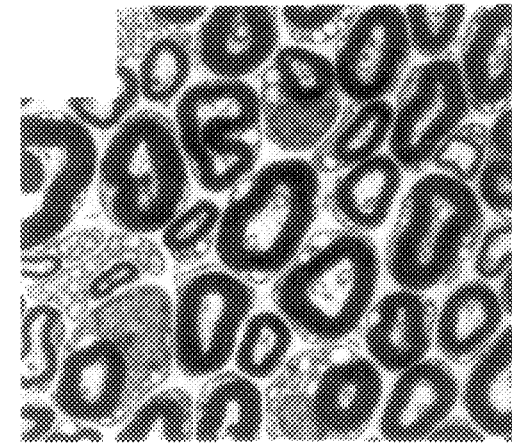

Microscopic examination of the sciatic nerve of NF-L −/− mice indicated that many myelinated axons were relatively hypermyelinated (FIG. 6E and F) as compared to those from NF-L +/− mice (C and D) or wild type mice (A and B). Quantitative analysis of ventral root fibers from ?-month old +/+, +/−, and −/− mice revealed a linear relationship between increasing axonal diameter and myelin thickness (FIG. 5B, D, F, H). The slope of the regression line for NF-L −/− mice differed from those obtained with NF-L +/− or +/+ mice, confirming that the peripheral axons in NF-L −/− mice have relatively thick myelin sheaths in proportion to axonal size.

EXAMPLE II

Use of Intermediate Filament Deficient Animal Model to Study Nerve Regeneration Deficient regeneration of peripheral axons lacking neurofilaments.

The immunoblots in FIG. 2A revealed a remarkable up-regulation of tubulin and GAP-43 proteins in homogenates from the cortex and sciatic nerve of both NF-L +/− and −/− mice. The Northern blots indicated that the increased protein levels of tubulin and GAP-43 in the NF-deficient mice are not due to changes in the mRNA levels; rather, they are due, at least in part, to enhanced rates of axonal transport of these proteins (data not shown).

Given that tubulin and GAP-43 are markers of axonal outgrowth (Kalil and Skine, (1986) *J. Neuroscience*) and that neurofilament mRNAs are down-regulated during the initial stages of nerve regeneration (Hoffman and Cleveland (1988) *Proc. Natl. Acad. Sci. USA*). Regeneration of PNS axons following axotomy in NF-deficient mice was examined in two- to three-month old homozygous −/−, heterozygous +/−, and wild type +/+ liter mates from six different litters. Both the sciatic nerve and the facial nerve were crushed. The sciatic nerve was crushed at the obturator tendon with #5 Dumon forceps either without (n=3) or with (n=3) prechilling in liquid nitrogen three times for 20 seconds. Facial nerve was crushed at a site behind the ear using #5 Dumont forceps at room temperature. A total of nine mice, three in each group, were used in the facial nerve regeneration studies. Animals were sacrificed at either 11 days (sciatic nerve) or 9 days (facial nerve) post-operation. The sciatic and facial nerves were dissected out and processed for light microscopy as described in EXAMPLE I above. Newly-regenerated myelinated axons were stained with Toludine blue, counted, and plotted as number per 10,000 square micrometer.

Figure 7G:
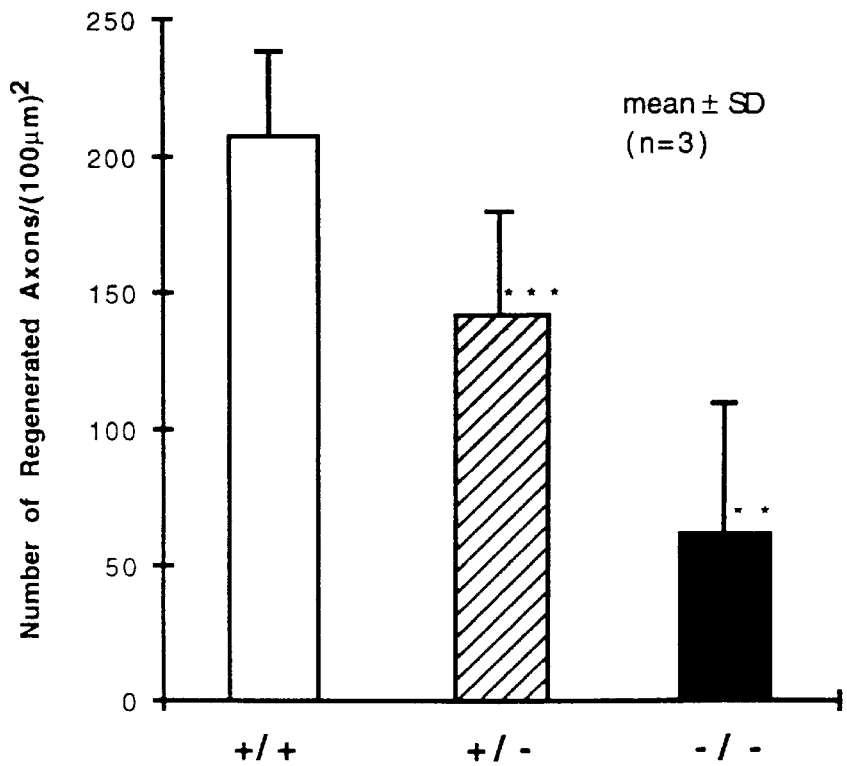
FIGS. 7(A–H). Regeneration of sciatic and facial nerves in NF-L knock-out mice. Cross-section of 3 mm distal region of sciatic nerve 11 days after a crush (A, C, E) and 9 mm distal region of facial nerve 9 days after a crush (B, D, F. Dark arrowheads point to newly regenerated axons and open arrowheads point to degenerating axons. The number of regenerated axons from three mice were counted and normalized as per 10,000 square micrometers for sciatic nerve (G) and facial nerve (H). A similar result was obtained using liquid nitrogen pre-chilled forceps. [Bar=10 $\mu$; $p<0.005$, $p<0.014$, *$p<0.09$.]
Figure 7H:
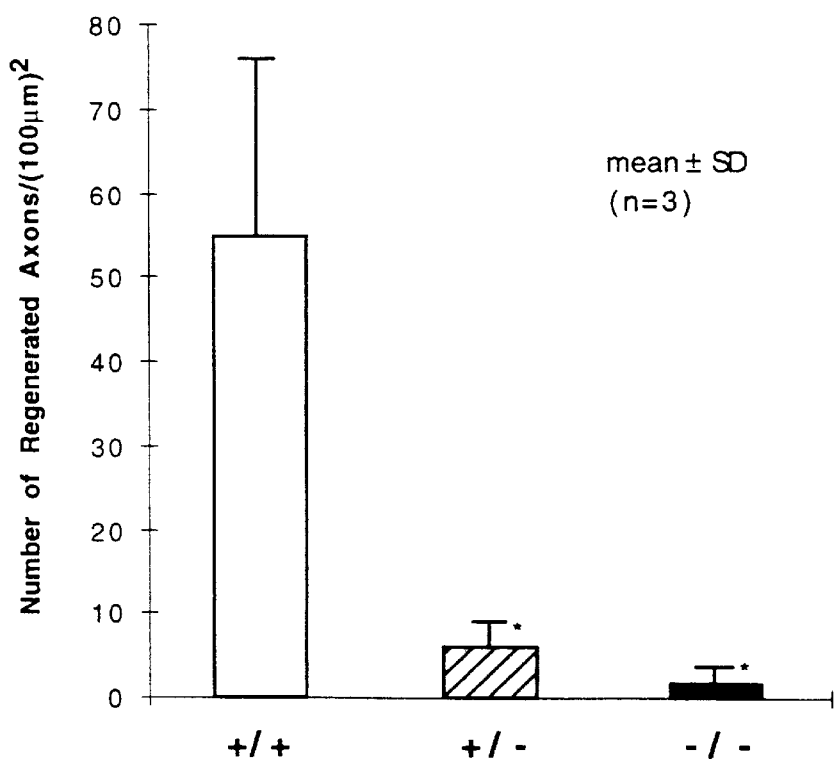

The micrographs in FIG. 7 represent cross-sections of the sciatic nerve 3 mm distal to the crush site from wild type +/+ (A), heterozygous +/− NF-L (C) and homozygous −/− NF-L (E) knock-out mice. As expected, numerous newly-regenerated axons (closed arrows) were detected 3 mm past the crush site of the sciatic nerve in normal mice. On average, approximately 200 regenerated axons per 10,000 $\mu^2$ were counted. These axons extended beyond 9 mm of the crush site in agreement with a regeneration rate of 4 mm/day reported for sciatic nerve axons (Tetzlaff and Bisby, (1989) Neuroscience, 29). In contrast, there was a very poor regeneration of sciatic nerve axons from the NF-L −/− mice (FIG. 7E). The number of newly-regenerated axons in NF-L −/− mice corresponded to approximately 10–30% of the number of regenerated axons observed in normal litter mates. No significant loss of myelinated axons was evident in the sciatic nerve region proximal to the axotomy site after 11 days, indicating that the lack of regenerated axons is not due to a rapid death of NF-L −/− neurons under conditions of stress. There was an intermediate degree of axonal regeneration in NF-L +/− mice indicating a correlation between axonal growth and neurofilament content.

The effect of neurofilament deficiency was even more dramatic following the crush of facial nerve in adult mice (2 months old). As shown in FIG. 7, less than 5% of the number of regenerated axons found in normal mice (B) was detected in NF-L −/− mice (F) at 3 mm distal to the crush site after 9 days. Moreover, the number of regenerated axons in the facial nerve of NF-L +/− mice was remarkably low and corresponded to about 10% of the number of regenerated axons observed in normal mice. Such a marked defect in mice lacking one NF-L allele was clearly unexpected; it is unlikely that this is the result of compensatory changes leading to robust inhibition of axonal growth. These results suggest that the neurofilament density in axons constitutes a critical intrinsic factor to allow efficient regeneration of adult axons.

Analysis of Study Using This Animal Model

Protein analysis and immunofluorescence studies indicated a marked decrease in all three neurofilament proteins in the nervous system of mice homozygous for the NF-L gene disruption. Electron microscopy further confirmed a lack of intermediate filaments in axons from the sciatic nerve and spinal cord. The reduced levels of NF-M and NF-H proteins in the absence of NF-L, which are not caused by changes in mRNA levels (FIG. 2A), probably result from changes in stability and/or axonal transport of these proteins due to the fact that they failed to polymerize into filaments. This is consistent with studies indicating that neurofilaments are obligate heteropolymers requiring NF-L in vivo (Ching and Liem, (1993) *J. Cell Biol.* 122:1323–1335; Lee et al. (1993) *J. Cell Biol.*, 122:1337–1350) and that purified NF-M or NF-H cannot self-polymerize into filaments in vitro (Hirokawa et al., (1984) *J. Cell Biol.*, 98:1523–1536).

The mechanism by which neurofilament proteins are transported down the axon following their synthesis in perikarya remains a controversial issue. The classical view that neurofilaments are transported as sliding polymer (Lasek et al. (1984) J. Cell Biol. 99:212–221) has been challenged by the detection of stationary and moving forms of neurofilament proteins (Nixon et al., (1986) J. Cell Biol., 102:647–659) and by photobleaching experiments demonstrating a segmental incorporation of subunits into axonal filaments (Okabe et al. (1993) J. Cell Biol. 121:375–386). The detection of small amounts of NF-M and NF-II proteins in NF-L −/− axons (FIG. 3) further supports the notion that polymer formation is not essential for transport of neurofilament proteins in vivo. The NF-L –/– mice provide a unique opportunity to investigate whether these subunits are transported as monomers or as small oligomeric structures, and whether the transport involves a microtubule-dependent mechanism or simple diffusion.

The hypotrophy of axons in the neurofilament-deficient knockout mice proves unequivocally that neurofilaments play a key role in the radial growth of axons. This is in agreement with a report of axonal hypotrophy in a Japanese quail mutant lacking neurofilaments as a result of a nonsense mutation in the NF-L gene (Yamasaki (1992) *Laboratory Investigation,* 734; Ohara (1993) *J. Cell Biol.,* 121:387–395). Reduced axonal calibers have also been observed in transgenic mice expressing a NF-H/ galactosidase fusion protein that interferes with neurofilament transport into axons (Eyer and Peterson (1994) *Neuron,* 12:389–405) and with various transgenic mice expressing abnormal ratios of neurofilament subunits (Xu et al., (1993) *Cell,* 73:23–33; Cote et al. (1993) *Cell,* 73:35–46; Collard et al. (1995) *Nature,* 375:61–64. While neurofilaments are clearly a major intrinsic determinant of axonal caliber, an analysis of NF-L +/– mice demonstrates that there is no direct correlation between neurofilament number and axon diameter; for example, a 50% decrease in the content of neurofilaments in myelinated axons of NF-L +/– mice (FIG. 4,C,D) provoked a modest 15% reduction in the calibers of ventral root axons (FIG. 5C). It is notable that the overexpression of any single neurofilament subunit in transgenic mice also provokes reduction of axon calibers (Monteiro et al. (1990) *J. Cell Biol.,* 111:1543–1557; Xu et al. (1993) *Cell,* 73:23; Cote et al. (1993) *Cell* 73:35–46).

The NF-L –/– mice develop no overt phenotypes. Although a modest 10% decline in the number of central root axons in NF-L –/– knockout mice was observed as compared to wild type (FIG. 5 G), the absence of pathology in NF-L –/– mice demonstrates that for most neurons the lack of neurofilaments is not, by itself, sufficient to alter nervous system development or function in mice. This situation contrasts with the obvious clinical signs in the NF-deficient quail mutant: this animal is characterized by a generalized quivering that begins immediately after hatching and continues throughout its life (Yamasaki et al. (1991) *Laboratory Investigation,* 82:734743.

From the foregoing description, one skilled in the art can easily ascertain the essential characteristics of this invention, and without departing from the spirit and scope thereof, can make various changes and modifications to the invention to adapt it to various usages and conditions. Consequently, such changes and modifications are properly, equitably, and intended to be within the full range of equivalence of the following claims.

The embodiments of the invention in which an exclusive property of privilege is claimed are defined as follows:

1. A method of producing a genetically engineered mouse in which the axons lack normal levels of a neuronal intermediate filament (NIF) protein selected from the group consisting of neurofilament light protein, neurofilament medium protein, and α-internexin, as compared to a wild type mouse comprising:

(a) transforming mouse embryonic stem cells with a DNA construct comprising a marker gene and at least 100 bp of DNA sequence homologous with a sequence of the endogenous NIF gene present in a chromosome of said embryonic stem cells, where said construct becomes integrated into said chromosome by homologous recombination, thereby inactivating said NIF gene;

(b) selecting for mouse embryonic stem cells which carry said inactivated NIF gene to provide selected cells;

(c) introducing the transformed embryonic stem cells into the blastocyst of a developing mouse embryo;

(d) allowing the embryo to develop to term;

(e) identifying at least one offspring which carries said inactivated NIF gene in the germ line; and (f) breeding said offspring to produce a homozygous or heterozygous mouse, wherein said mouse displays at least a 50% reduction in the expression of said NIF gene which results in axons lacking the normal levels of said NIF protein in its axons.

2. A method of producing a genetically engineered mouse with neurons lacking the normal levels of a NIF protein selected from the group consisting of neurofilament light protein, neurofilament medium protein, and α-internexin, as compared to a wild type mouse, said method comprising transforming mouse embryonic stem cells with a DNA construct comprising a marker gene and at least 100 bp of DNA sequence homologous with a gene sequence for the endogenous mouse NIF gene, introducing said embryonic stem cells into the blastocyst of a developing mouse embryo, and allowing said embryo to develop to term to result in a mouse having at least a 50% reduction in the expression of said NIF gene and resulting in a mouse in which the axons lack the normal levels of said NIF protein, as compared to a wild type mouse.

3. A genetically engineered mouse which has at least a 50% reduction in the expression of an endogenous NIF gene selected from the group consisting of the neurofilament light gene, the neurofilament medium gene, and the α-internexin gene which results in axons of the mouse lacking the normal levels of the encoded NIF protein, as compared to a wild type mouse, said mouse being produced by the method of either of claims 1 or 2.

4. The mouse according to claim 3, wherein said NIF is neurofilament light protein.

5. The mouse according to claim 3, wherein said NIF is neurofilament medium protein.

6. The mouse according to claim 3, wherein said NIF is α-internexin.

* * * * *